(12) United States Patent
Galdonik et al.

(10) Patent No.: US 8,409,237 B2
(45) Date of Patent: *Apr. 2, 2013

(54) EMBOLI FILTER EXPORT SYSTEM

(75) Inventors: Jason A. Galdonik, Hanover, MN (US);
Matthew F. Ogle, Oronoco, MN (US);
James Pokorney, Northfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 1514 days.

This patent is subject to a terminal disclaimer.

(21) Appl. No.: 10/854,920

(22) Filed: May 27, 2004

(65) Prior Publication Data

US 2005/0277976 A1 Dec. 15, 2005

(51) Int. Cl.
*A61M 29/00* (2006.01)

(52) U.S. Cl. .................................. 606/200

(58) Field of Classification Search ............ 606/200
See application file for complete search history.

(56) References Cited

U.S. PATENT DOCUMENTS

| | | | |
|---|---|---|---|
| 4,610,662 A | 9/1986 | Weikl et al. | |
| 4,723,549 A | 2/1988 | Wholey et al. | |
| 4,728,319 A | 3/1988 | Masch | |
| 4,784,636 A | 11/1988 | Rydell | |
| 4,790,812 A | 12/1988 | Hawkins, Jr. et al. | |
| 4,794,928 A | 1/1989 | Kletschka | |
| 4,873,978 A | 10/1989 | Ginsburg | |
| 4,883,460 A | 11/1989 | Zanetti | |
| 4,887,613 A | 12/1989 | Farr et al. | |
| 4,994,067 A | 2/1991 | Summers | |
| 5,011,488 A | 4/1991 | Ginsburg | |
| 5,011,490 A | 4/1991 | Fischell et al. | |
| 5,053,008 A | 10/1991 | Bajaj | |
| 5,059,178 A | 10/1991 | Ya | |
| 5,102,415 A | 4/1992 | Guenther et al. | |
| 5,108,419 A | 4/1992 | Reger et al. | |
| 5,152,277 A | 10/1992 | Honda et al. | |

(Continued)

FOREIGN PATENT DOCUMENTS

| | | |
|---|---|---|
| WO | WO 95/05209 | 2/1995 |
| WO | WO 98/38930 | 9/1998 |

(Continued)

OTHER PUBLICATIONS

Feldman, "Transcatheter Aspiration of a Thrombus in an Aortocoronary Saphenous Vein Graft," Am. J. Cardiol. Aug. 1, 1987, 60(4), 379-380.

(Continued)

*Primary Examiner* — Gary Jackson
*Assistant Examiner* — Michael Mendoza (57) ABSTRACT

Methods for the removal of an embolism protection device use aspiration during the drawing of the embolism protection device into the catheter. Generally, the embolism protection device comprises a three dimensional filtering matrix that provides improved filtering without blocking the flow through the patient's vessel. In some embodiments, the embolism protection device can be actuated between a deployed configuration and a removal configuration with a reduced area across the cross section of the vessel lumen. The embolism protection device in the removal configuration can be drawn within the aspiration catheter. The aspiration catheter can have a distal portion with an expanded compartment with an average diameter at least about 20 percent larger than the average diameter of the shaft of the catheter within about 10 centimeters of the expanded compartment. In a rapid exchange version, the rapid exchange segment can have a length of at least about 10 centimeters.

8 Claims, 7 Drawing Sheets

U.S. PATENT DOCUMENTS

| | | | |
|---|---|---|---|
| 5,163,906 | A | 11/1992 | Ahmadi |
| 5,211,651 | A | 5/1993 | Reger et al. |
| 5,549,626 | A | 8/1996 | Miller et al. |
| 5,599,307 | A | 2/1997 | Bacher et al. |
| 5,766,191 | A | 6/1998 | Trerotola |
| 5,814,064 | A * | 9/1998 | Daniel et al. .................. 606/200 |
| 5,827,229 | A | 10/1998 | Auth et al. |
| 5,836,868 | A | 11/1998 | Ressemann et al. |
| 5,843,051 | A | 12/1998 | Adams et al. |
| 5,897,567 | A | 4/1999 | Ressemann et al. |
| 5,910,154 | A * | 6/1999 | Tsugita et al. ................ 606/200 |
| 5,911,725 | A | 6/1999 | Boury |
| 5,911,734 | A | 6/1999 | Tsugita et al. |
| 5,938,645 | A | 8/1999 | Gordon |
| 5,941,869 | A | 8/1999 | Patterson et al. |
| 5,997,557 | A | 12/1999 | Barbut et al. |
| 6,010,522 | A | 1/2000 | Barbut et al. |
| 6,022,336 | A | 2/2000 | Zadno-Azizi |
| 6,135,991 | A | 10/2000 | Mini et al. |
| 6,142,987 | A | 11/2000 | Tsugita |
| 6,159,195 | A | 12/2000 | Ha et al. |
| 6,168,579 | B1 | 1/2001 | Tsugita |
| 6,203,561 | B1 | 3/2001 | Ramee et al. |
| 6,206,868 | B1 | 3/2001 | Pariodi |
| 6,270,477 | B1 | 8/2001 | Bagaoison et al. |
| 6,361,545 | B1 | 3/2002 | Macoviak et al. |
| 6,454,741 | B1 | 9/2002 | Muni et al. |
| 6,485,500 | B1 | 11/2002 | Kokish |
| 6,485,502 | B2 * | 11/2002 | Don Michael et al. ....... 606/200 |
| 6,527,746 | B1 * | 3/2003 | Oslund et al. .................. 604/160 |
| 6,562,058 | B2 * | 5/2003 | Seguin et al. .................. 606/200 |
| 6,569,148 | B2 | 5/2003 | Bagaoisan et al. |
| 6,596,011 | B2 | 7/2003 | Johnson et al. |
| 6,602,271 | B2 * | 8/2003 | Adams et al. .................. 606/200 |
| 6,620,148 | B1 | 9/2003 | Tsugita |
| 6,706,055 | B2 * | 3/2004 | Douk et al. .................... 606/200 |
| 6,805,692 | B2 | 10/2004 | Muni et al. |
| 6,911,036 | B2 | 6/2005 | Douk et al. |
| 7,229,464 | B2 | 6/2007 | Hanson et al. |
| 7,717,934 | B2 * | 5/2010 | Kusleika ........................ 606/200 |
| 8,092,483 | B2 * | 1/2012 | Galdonik et al. ............. 606/200 |
| 2002/0035347 | A1 | 3/2002 | Bagaoisan |
| 2002/0169472 | A1 | 11/2002 | Douk et al. |
| 2003/0023263 | A1 | 1/2003 | Krolik et al. |
| 2003/0135232 | A1 | 7/2003 | Douk et al. |
| 2004/0006365 | A1 | 1/2004 | Brady et al. |
| 2004/0254602 | A1 | 12/2004 | Lehe et al. |
| 2005/0021075 | A1 | 1/2005 | Bonnette et al. |

FOREIGN PATENT DOCUMENTS

| | | |
|---|---|---|
| WO | WO 02/085092 | 10/2002 |

OTHER PUBLICATIONS

Nakagawa et al., "A Retrievable Nitinol Vena Cava Filter: Experimental and Initial Clinical Results," J. of Vascular and Interventional radiology, May-Jun. 1994; 5:507-512.

\* cited by examiner

EMBOLI FILTER EXPORT SYSTEM

FIELD OF THE INVENTION

The invention relates to catheters for the removal of emboli traps, i.e. embolism protection devices. In particular, the invention relates to aspiration catheters that facilitate the removal of an embolism protection device, which can have a three-dimensional filtering matrix, from a patient's vessels with reduced or eliminated release of emboli. The invention further relates to improved aspiration catheters that are capable of rapid exchange, which can form a protective lumen for a three-dimensional filtering matrix during removal from the patient.

BACKGROUND OF THE INVENTION

An embolus can be any particle comprising a foreign and/or native material, which enters the vascular system or other vessel of the body with potential to cause occlusion of blood flow. Emboli can be formed from aggregates of fibrin, blood cells or fragments thereof, collagen, cholesterol, plaque, fat, calcified plaque, bubbles, arterial tissue, and/or other miscellaneous fragments or combinations thereof. Emboli can lodge in the narrowing regions of medium size blood vessels that feed the major organs. Loss of blood flow to surrounding tissue causes localized cell death or microinfarcts. Cerebral microinfarcts can cause stroke leading to confusion, disturbance of speech, paralysis, visual disturbances, balance disturbances and even death. In the heart, emboli can cause myocardial infarcts, i.e. heart attacks. Myocardial infarction refers to the death of a section of myocardium or middle layer of the heart muscle. Myocardial infarction can result from at least partial blockage of the coronary artery or its branches. Blockage of capillaries associated with the coronary arteries can result in corresponding microinfarctions/microinfarcs. Resulting impairments are frequently short term but can be permanent.

Disease states including arteriosclerosis and deep vein thrombosis, aging and even pregnancy can cause build up of plaque and fibrin on vessel walls. Anything that loosens or breaks up this plaque can generate emboli. The clinical ramifications of emboli are staggering. Emboli generated from arteriosclerosis of the carotid artery alone cause 25% of the 500,000 strokes that occur yearly in the United States (2002 American Heart Association And Stroke annual statistics).

Many clinical procedures can result in emboli including, for example, coronary, carotid, and peripheral interventions. In these cases, particulate matter, including, for example, plaque, debris and thrombus, can form emboli distal to the site of intervention. As a result, blood flow to the distal vascular bed can be diminished and periprocedural end-organ ischemia and infarction can result. Distal embolization of large particles produced at the time of such interventions as balloon inflation or stent deployment may obstruct large, epicardial vessels, and smaller particles (as small as 15-100 microns) can cause microinfarcts and/or myocardial infarctions and left ventricular dysfunction.

Each year there are approximately 800,000 cardiac surgical cases, which involve cardiopulmonary bypass (CPB) worldwide. Of these cardiac surgical cases, approximately 48,000 suffer stroke and nearly 300,000 experience some neurocognitive disturbance. This is a significant clinical problem. These complications are due in large measure to CPB-generated emboli. The average number of emboli measured by Trans Cranial Doppler (TCD) in patients undergoing cardiopulmonary bypass is 183 (range 3-947). The majority of emboli end up in the very distal cerebral tree, the terminal arterioles and capillaries causing microinfarctions, (i.e., loss of blood flow to surrounding tissue).

Ironically, the surgical interventions used to remove or bypass the plaque of arteriosclerosis (e.g., balloon dilatation angioplasty, endarterectomy, bypass grafting and stenting) can themselves disrupt plaque. One of the most common cardiovascular interventions is coronary artery bypass grafting (CABG). Historically, 10-20% of all CABG interventions generate emboli large enough to cause myocardial infarcts. This is particularly true when the graft used is of saphenous vein origin. But CABG is not the only procedure with potential to generate emboli. In fact, doppler ultrasound shows evidence of microembolization in almost all cardiac intervention cases. Of the over 1.8 million intervention procedures performed annually, greater than 10% result in neurocognitive disturbance and/or ischemic event. These impairments are frequently short term, but can be permanent.

Ten percent is currently considered an acceptable complication rate, however as the number of procedures continues to grow (15-35% increase annually depending on specific procedure (Medical And Healthcare Marketplace Guide, 17th Edition Volume 1, Research Reports 2001-2002, incorporated herein by reference.) the total number of patients affected grows. As this number increases so does patient care spending. While daunting, cost figures fail to include the social and financial burden placed on family members upon hospital release. In summary, embolic events complicating percutaneous endovascular procedures cause high rates of clinically observed neurological disturbances and cardiovascular disease, decreased quality of life and increased patient care spending. Thus, there is a significant clinical need for effective prevention of adverse embolic events.

A significant reason for ischemic injury during percutaneous procedures can be generation of emboli which block smaller distal vessels. One approach to curb this complication has been to use pharmacological therapies during the time of the intervention. Limited therapeutic success has been reported with the use of calcium channel blockers, adenosine, and sodium nitroprusside (Webb, J G, Carere, R G, Virmani, R, Baim, D, Teirstein, P S, Whitlow, P, McQueen, C, Kolodgie, F D, Buller, E, Dodek, A, Mancini, G B, & Oesterle, S: Retrieval and analysis of particulate debris after saphenous vein graft intervention. *J Am Coll Cardiol* 2000, 34:468-475, incorporation herein by reference). Glyoprotein IIb/IIIa inhibitors have been used for percutaneous coronary interventions to reduce platelet aggregation, but also fail to show meaningful long term clinical benefit. (Mathew, V, Grill, D E, Scott, C G, Grantham, J A, Ting, H H, Garratt, K N, & Holmes, D R, Jr. The influence of abciximab use on clinical outcome after aortocoronary vein graft interventions. *J Am Coll Cardiol* 1999, 34:1163-1169 and Mak, K H, Challapalli, R, Eisenberg, M J, Anderson, K M, Califf, R M, & Topol, E J: Effect of platelet glycoprotein IIb/IIIa receptor inhibition on distal embolization during percutaneous revascularization of aortocoronary saphenous vein grafts. EPIC Investigators. Evaluation of IIb/IIIa platelet receptor antagonist 7E3 in Preventing Ischemic Complications. *Am J Cardiol* 1997, 80:985-988, both of which are incorporated herein by reference.) Since embolization often develops from physical disruption of fibrotic plaque, a mechanism of therapeutic embolic protection specifically targeted at prevention of platelet aggregation and blood clotting may have little effect on these already-formed, embolizable plaques.

Surgical procedures for the treatment of renal artery stenosis can also generate emboli. There is clinical evidence to suggest that 36% of those treated suffer arterioloar nephrosclerosis caused by atheroemboli. Five-year survival of patients with atheroembolic events is significantly worse than of patients without atheroemboli (54% vs. 85% respectively) [Krishmamurthi et al. J Urol. 1999, 161:1093-6]. These patients could also benefit from distal protection devices.

Foreign material in the stream of flow can cause turbulence or low flow. Such flow conditions have been shown to increase rates of infection. Thrombus not only generates emboli, but also increases the risk of infection. (9)

It is evident that a wide variety of embolic events cause high rates of clinically observed symptoms, decreased quality of life and increased patient care spending. Filtering devices can collect some or all emboli of concern from a particular flow. However, in most cases, the device is removed at some point from the flow, generally after the causes of an embolic event are no longer present. The removal of the device from the patient can disrupt the device in a way that can result in release of some of the emboli from the device. Any released emboli can flow down stream and pose a risk to the patient.

SUMMARY OF THE INVENTION

In a first aspect, the invention pertains to a method for the removal of an embolism protection device from a patient's vessel. The method comprises drawing an embolism protection device within an aspiration catheter while applying suction through the aspiration catheter. The embolism protection device has a three dimensional filtering matrix.

In another aspect, the invention pertains to a method for the removal of an embolism protection device from a patient's vessel in which the method comprises drawing an embolism protection device within an aspiration catheter while applying suction through the catheter. The drawing of the embolism protection device into the aspiration catheter comprises converting the embolism protection device from an expanded configuration across the lumen of a vessel to a recovery configuration with a reduced area across the cross section of the vessel lumen. The converting of the embolism protection device comprises disengaging an actuating element that expands the embolism protection device to an expanded configuration.

In another aspect, the invention pertains to an aspiration catheter comprising a suction device, a proximal portion, a distal portion and a shaft connected between the distal portion and the proximal portion. The suction device is attached to the proximal portion to supply suction to the distal portion through a continuous lumen extending from the proximal portion to the distal portion. The distal portion comprises an expanded compartment with an average diameter at least about 20% larger than the average diameter of the shaft within about 10 centimeters of the expanded compartment, and the distal portion has a distal opening also at least about 20% larger than the average diameter of the shaft.

In another aspect, the invention pertains to a rapid exchange aspiration catheter comprising a suction device, a proximal portion, a rapid exchange segment having a distal end and a shaft attached between the proximal portion and the rapid exchange segment. Generally, the rapid exchange segment comprises a port adjacent the connection between the shaft and the rapid exchange segment with the distal portion having a larger average diameter than the shaft. The suction device is attached to the proximal portion to supply suction at the distal end through a continuous lumen extending from the proximal portion to the distal portion. In embodiments of particular interest, the rapid exchange segment has a length of at least about 10 centimeters.

In some embodiments of particular interest, the aspiration catheter has a single lumen design. For a single lumen design, the distal port, which captures the embolic filter, the side port, which functions as an exit port for a guidewire, and the proximal suction port share the same lumen. The side exit port can be sized such that the diameter of the corresponding wire fills the majority of the diameter of the port to enable suction to occur at the distal tip. Also, to guide the wire to the side port during loading, a small thin walled loading tube may be used. This tube tracks the wire into the major lumen and out the side port. After loading, the tube can be removed and generally discarded. In alternative embodiments, multiple lumens can be used to facilitate loading and to isolate the side port from suction.

Furthermore, the invention pertains to a kit for an embolism protection system comprising a guidewire, an embolism protection device having an expanded configuration with a three dimensional filtering matrix and a recovery configuration, and an aspiration catheter. Generally, the aspiration catheter comprises a distal compartment with an appropriate size and configuration to accept the embolism protection device in the recovery configuration.

DETAILED DESCRIPTION OF THE INVENTION

An improved system for trapping and removing emboli from a patient involves an aspiration catheter that, in some embodiments, both transmits suction to the distal end of the catheter to aspirate liquid into the catheter as well as provides a protective lumen in which to draw the embolism protection device for removal from the patient. Thus, for removal, the embolism protection device can be drawn within the catheter while aspiration is applied. The aspiration catheter then functions as a vehicle for the removal of the embolism protection device. The use of suction along with the sheath catheter system can significantly reduce or eliminate the release of any emboli during the removal of the embolism protection device. In some embodiments, the aspiration catheter comprises an expanded compartment into which the embolism protection device is drawn in a recovery configuration. In some embodiments, the embolism protection device comprises a three dimensional filtering matrix that provides a flow network that is less likely to clog with emboli during filtering and generally does not occlude flow while deployed or suction during recovery. In some embodiments of particular interest, the three dimensional filtering matrix comprises fibers, such as surface capillary fibers. The fibers can be attached to the distal end of a guidewire. The aspiration catheter can be an over the wire structure or a rapid exchange design. In particular, the rapid exchange aspiration catheter can be a single lumen design. While many of the devices are particularly suited for incorporation into a system for embolism protection, some of the devices are suitable for a range of additional medical applications.

Embolism protection devices can be delivered in response to a variety of circumstances. For example, the device can be delivered prior to performance of a medical procedure that has the potential of resulting in the release of emboli. Similarly, one or more devices can be implanted following an injury or trauma that can result in the formation and/or release of emboli. In addition, one or more devices can be implanted in an individual that had developed a physiological condition in which emboli may develop. The devices can be used in conjunction with other therapeutic device(s) and/or therapy such as drug therapy.

Regardless of the circumstances in which the device is implanted, many embodiments subsequently have indications calling for the subsequent removal, i.e., recovery, of the device. Recovery can be performed, for example, after conclusion of a specific medical procedure, after a particular risk has passed or in conjunction with the placement of another replacement embolism protection device. Manipulating the embolism protection device can create a risk associated with dislodging emboli entrapped in the device and release of the emboli into the patient's fluid flow, whether blood or other fluid. The devices and procedures described herein facilitate the removal of an embolism protection device with reduced or eliminated loss of trapped emboli during the removal of the device. The devices and procedures can be used with respect to embolism protection devices that are not attached after delivery or embolism protection devices that remain attached after delivery. These procedures and apparatuses are generally used on mammalian patients, in particular humans. Similarly, these devices can be used in any blood vessel, urinary vessel or other vessel of the patient.

In some embodiments, the embolism protection systems and corresponding processes described herein make use of aspiration catheters for the retrieval of an embolism protection device from a vessel in a patient. Several improved design features are described herein for aspiration catheters. In general, embolism protection systems provide for the delivery and deployment of the embolism protection device, recovery of the embolism protection device and possibly the deployment of additional treatment structures. To accomplish these functions, the system generally comprises one or more guidewires, an embolism protection device, an aspiration catheter, optional sheaths for the delivery of the embolism protection device, a delivery tool, a recovery tool and other optional components. In some embodiments, one or more of these components of the system can be integrated together. In particular, for embodiments in which the embolism protection device remain attached during use, it is possible to use a single guide wire as well as combine the delivery tool and recovery tool. In addition, for attached or tethered embodiments, the embolism protection device can be integrated with other components, specifically, the guidewire, delivery tool and recovery tool.

In particular, embolism protection systems can provide for the delivery of an embolism protection device, for the deployment of the embolism protection device and for the recovery of the embolism protection device with components that are designed for operation in cooperation with each other. In some embodiments of interest, the system can provide for the delivery of the embolism protection device attached to a guidewire, hypotube or the like and actuation of the device to deploy the embolism protection device within the patient's vessel. The guidewire/hypotube can then be used to deploy treatment devices such as stents, angioplasty balloons and the like. Then, an aspiration catheter can be delivered using the same guidewire/hypotube for the removal of the embolism protection device. Such an integrated system can be very effective at efficient delivery of treatment within a vessel with the protection of an embolism protection device while providing for the efficient and safe removal of the embolism protection device.

The aspiration catheter can provide suction at the distal end of the aspiration catheter. In addition, the aspiration catheter can have a specific compartment at its distal end for the withdrawal of the embolism protection device such that the compartment functions as a sheath for the embolism protection device as the device is withdrawn. Generally, a suitable compartment can be a distal portion with an enlarged diameter. The suction is generally delivered with an appropriate suction device, such as a syringe or pump, that is connected at the proximal end of the aspiration catheter. For these embodiments, there is an open lumen extending through the catheter from the proximal end to the distal end.

The aspiration catheter can be delivered to an appropriate location near a deployed embolism protection device. The aspiration catheter and/or the embolism protection device can comprise a radio-opaque marker to facilitate the positioning of devices within the patient and relative to each other. The aspiration catheter can be an over the wire design in which the catheter runs over the wire along the entire length of the catheter. In alternative embodiments, the aspiration catheter has a rapid exchange design. For the rapid exchange designs, a port provides for the transition of the wire out from the catheter. In some embodiments, a channel or open lumen extends from the proximal to the distal ends. For these embodiments, it can be challenging to direct the wire to the port. A grid or the like can be placed over the opening of the lumen near the port to guide the wire to the port without obstructing flow through the catheter during use. Multiple lumens can be constructed such that the wire follows a major lumen out through the side port. Alternatively or additionally, a tube can be inserted temporarily through the port. The wire can be directed through the port in the tube. Once the wire is through the port, the tube can be removed.

A range of designs of the embolism protection device are suitable can be incorporated into the systems described herein. Embolism protection devices with a three dimensional filtering matrix can provide particularly desirable properties. In particular, the filtering matrix can entrap larger emboli on its surface and smaller emboli within the matrix to provide improved filtering with less occlusion of flow. The filter furthermore provides a distribution of effective pore sizes. In addition, a three dimensional filtering matrix generally does not block suction while the device is converted to a recovery configuration. In fiber based filters described herein, the fiber structures can facilitate fluid motion while trapping small emboli. The three dimensional matrices generally have considerable flexibility to conform to the vessel wall shape to effectively prevent gaps larger than the effective pore sizes of the filter. Also, the three dimensional filters have considerable filtering capacity without becoming blocked. Thus, embolism protection devices with a three dimensional filtering matrix can provide improved performance during filtering and/or during removal. Also, it can be desirable to include a radio-opaque marker on the embolism protection device to facilitate positioning of the device.

Certain designs of the embolism protection device can be particularly suitable. For example, in some embodiments, the embolism protection device can be self-expandable upon deployment into a patient's vessel. Such embolism protection devices can comprise polymers that help to effectuate the desired expansion. Specifically, the embolism protection device can comprise a swellable polymer, such as a hydrogel, a shape memory polymer or the like. In some embodiment, the embolism protection device comprises surface capillary fibers. Surface capillary fibers are particularly desirable since they are able to trap smaller emboli within the surface capillaries and larger emboli between the fibers for extremely effective filtering of emboli. The surface capillary fibers can be used in a bundle within the embolism protection device. The number and properties of the fibers can be selected to trap emboli with selected properties while permitting desired flow through the vessel. In embodiments, of interest, the embolism protection device provided for little if any resistance to flow through the vessel.

In some embodiments of interest, the embolism protection device is attached at or near the end of a core wire that is part of an integrated guiding device. The embolism protection device is then delivered within the vessel with the steerable integrated guiding device. The integrated guiding device can also be used to actuate deployment of the embolism protection device. Suitable integrated guiding devices for actuation of the embolism protection device can comprise a hypotube over a core wire. The hypotube can have an outer diameter approximately equal to the outer diameter of a conventional guidewire such that treatment structures, such as angioplasty balloon or stent, can be delivered over the same integrated guiding device used to deploy the embolism protection device. To facilitate the conveyance of torque along the core wire, the hypotube and core wire can be rotationally coupled, at least at selected times. In these embodiments, the core wire can be steered by rotating the hypotube. The structures can be designed to provide for longitudinal movement of the hypotube relative to the core wire for actuation of the embolism protection device.

In some embodiments, the embolism protection device comprises a bundle of surface capillary fibers attached at their distal end to a core wire. At their proximal end, the fibers are attached to the hypotube separated from the core wire by a tube that rides over the core wire. In these embodiments, moving the hypotube longitudinally in a distal direction relative to the core wire brings the two ends of the fibers together flaring outward the center of the fibers. Then, the flared fibers can extend across the vessel lumen to filter flow passing through the vessel. To recover the embolism protection device, the fibers can either be distorted into compressed configuration by bending into a sheath to enclose the embolism protection device during recovery, or the device can be extended to a configuration with the fibers more extended. The fibers can be extended for removal by translating the sheath in a proximal direction relative to the core wire essentially to un-deploy the embolism protection device.

In embodiments in which the embolism protection device is un-attached following delivery, a gripping device can be employed to facilitate recovery of the device. The gripping device can be used to compress the device to a smaller configuration for withdrawal into a sheath for removal. The gripping device can be actuated from the distal end of a shaft that supports the gripper at the distal end. Suction can be applied during the gripping process and/or while the device is being withdrawn into a sheath for removal.

Once a guidewire, hypotube or the like is in place, whether or not connected to the embolism protection device, various treatment structures can be delivered to upstream locations relative to the embolism protection device for the performance of desired treatment. Suitable treatment structures include, for example, angioplasty balloons, stents, and the like. These treatment devices can be inserted over the guidewire, hypotube or other appropriate structure.

In general, the delivery and deployment of the embolism protection device is dictated by medical indications that suggest the desirability of the protection afforded by the embolism protection device. In some situations, an embolism protection is deployed for an extended period of time without any tethering or other attachment of the device. For example, the device can be deployed for periods of hours, days, weeks, months or possibly even longer. For example, longer term deployment can be suitable following a trauma that can result in embolic formation until the trauma injury has sufficiently healed. The procedures and apparatuses described herein can be employed to remove the embolism protection device at the selected time.

In other embodiments, the embolism protection device remains attached or tethered during use. In these embodiments, the time of deployment is generally relatively short. Specifically, for these embodiments, the embolism protection device can be deployed shortly before the performance of a particular treatment procedure. Then, the embolism protection device may be left in for a short period after the treatment is completed, and removed thereafter. The tether or other attachment structure itself can be used to facilitate the removal of the device.

In general, for any of the various embodiments, at some point in time, it may be desirable to remove the embolism protection device from the patient. In order to avoid negating at least some of the beneficial effects of the embolism protection device, it is desirable to avoid release of emboli during the recovery of the embolism protection device. Suction alone or combined with covering the embolism protection device in a sheath can be used to reduce or eliminate release of emboli from the embolism protection device during recovery.

Generally, suction can be applied as the embolism protection device is transformed from a deployed configuration to a configuration with a narrower profile for withdrawal. The embolism protection device can be transformed from the deployed configuration with an actuator, such as a hypotube-core wire integrated system, that directly converts the device from the deployed configuration to a recovery configuration. Alternatively or additionally, the embolism protection device can be mechanically compressed into a recovery configuration. In the recovery configuration, the device does not extend across the cross section of the vessel lumen such that it can be withdrawn from the vessel, generally along a guidewire and/or catheter. In some embodiments, a sheath is used as a protective lumen for the embolism protection device in the recovery configuration. The sheath for removal of the embolism protection device generally is provided as a compartment at the distal end of an aspiration catheter. Once the embolism protection device is compacted into its recovery configuration and, if relevant, drawn into a sheath, the embolism protection device and aspiration catheter can be withdrawn from the patient's vessel. Suction can be applied a short period of time prior to compacting the embolism protection device, during compaction of the embolism protection device, while drawing the embolism protection device into the sheath, for portion of the period of withdrawing the embolism protection device, and/or for selected portions of any or all of the steps in the removal process for the embolism protection device.

Improved designs of aspiration catheters described herein provide for improved recovery of an embolism protection device by combining aspiration with withdrawal of the device into a sheath for removal. When combined with the selection of appropriately effective embolism protection devices, the systems and procedures herein can effectively filter emboli without restricting flow through the vessel and can provide for removal of the device without significant release of emboli into the flow. Throughout this procedure, the deployment, use and removal of the embolism protection device only results in obstruction of the flow for a brief period in which suction is applied during withdrawal of the embolism protection device into the sheath. Thus, an efficient, easy to use and effective approach is provided for providing embolism protection and restoring the patient to a pre-procedure condition.

Embolic Protection System and Aspiration Catheter

In general, an embolic protection system can comprise an embolism protection device, optional treatment systems, suitable delivery components, and suitable recovery components, which may or may not have elements in common. The delivery components generally comprise a guidewire or the like and appropriate apparatuses to transport the embolism protection device to the delivery location. Similarly, the recovery components can comprise a guidewire or the like and appropriate apparatuses to recover the embolism protection device, although one or more components can be the same elements that are used for delivery of the device. Specifically, for unattached embolism protection devices, some of the delivery components may or may not be the same as some of the components used for device recovery. For embodiments in which the embolism protection device remains attached, the delivery components generally have elements in common with the components used for device recovery. In general, the recovery components comprise an aspiration catheter. Specific designs of embolism protection devices are described further in the following headed section. Also, a specific integrated system for deployment and recovery of a fiber based embolism protection device is described below.

Figure 1:
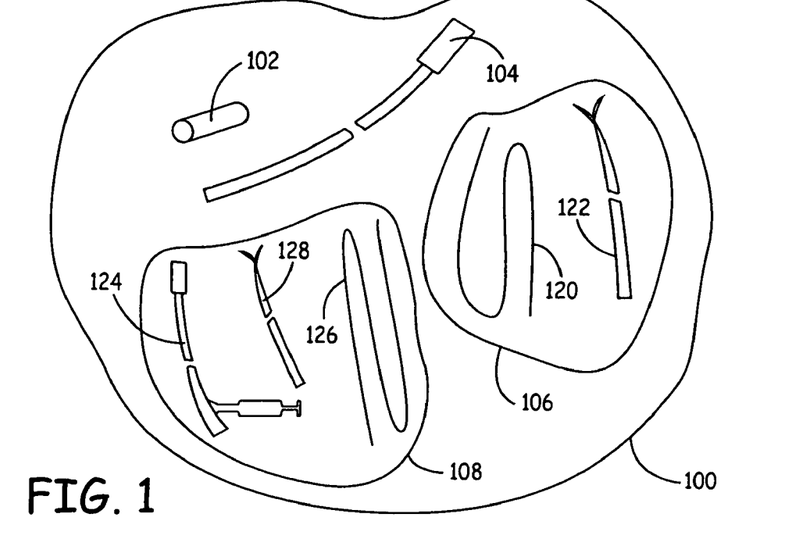
FIG. 1 is a schematic representation of a system for the delivery, use and recovery of an embolism protection device.

An embolic protection system 100 is shown schematically in FIG. 1. In some embodiments, embolism protection system 100 comprises an embolism protection device 102, an optional treatment system 104, delivery components 106 and recovery components 108. Suitable embolism protection devices 102 are discussed below. Treatment systems 104 can be any suitable treatment device suitable for percutaneous delivery to treat a blockage of patient's vessel, an aneurysm or other condition in a vessel. Suitable treatment systems include, for example, angioplasty balloons, stents, and tools for mechanically disrupting plaque. Suitable angioplasty balloons are described further, for example in U.S. Pat. No. 6,132,824 to Hamlin, entitled "Multilayer Catheter Balloon," incorporated herein by reference. Stent delivery is described further, for example, in U.S. Pat. No. 6,610,069 to Euteneuer et al., entitled "Catheter Support For Stent Delivery," incorporated herein by reference. Various stents and angioplasty balloons are commercially available.

In general, delivery components 106 comprise a guidewire 120 and a delivery tool 122 that can transport the embolism protection device within the patient's vessel to a delivery location. The embolism protection device can be deployed with a syringe, catheter, cannula, grippers or other convenient approach. Several specific approaches are described herein, and a person of ordinary skill in the art can adapt other delivery approaches based on the teachings herein. In some embodiments, a conventional guidewire can be used. Various commercial guidewires are available, such as Hi-Torque Spatacore™ guidewire with a stainless steel shaft with a 0.014 inch outer diameter, a special flexible tip design and a low friction coating, available from Guidant, Indianapolis, Ind. Below, an integrated guide device, as an alternative to a conventional guidewire, is described as a specific embodiment. Delivery tool 122 can interface with guidewire 120 to guide the embolism protection device to the delivery location. In alternative embodiments, guidewire 120 can be used to position a catheter, and delivery tool 122 can be delivered through the catheter with or without the removal of the guidewire. In some embodiments, the delivery tool is integrated with the guidewire, such that a single device incorporates both features. The delivery tool can be, for example, sheaths, cannulas, and gripping tools. The embolism protection device can be placed within a cannula to enclose the device for delivery.

Similarly, recovery components 108 can comprise an aspiration catheter 124, a guidewire 126 and a recovery tool 128 that can grip and remove the embolism protection device from a deployed configuration within a patient's vessel. These components can be same or different from the corresponding delivery components. Similarly, in some embodiments, the guidewire and the recovery tool can be integrated together into a single device. The guidewire can have various designs and compositions including, for example, conventional designs and compositions. Since the embolism protection device expands to contact the interior of the vessel walls, it may be desirable to introduce structures that facilitate the removal of the device. If the device remains attached to the delivery tool, the delivery tool can similarly be used to facilitate extraction of the device, although in some embodiments, as described below, an actuation device can convert the embolism protection device to a configuration suitable for removal without mechanical compaction of the device with a recovery tool. In other embodiments, the embolism protection device is left for some period of time within the patient's vessel, and a recovery tool can be used to recover the device. The recovery tool can be, for example, grippers or a coil structure that compacts the embolism protection device through rotation. The relationship between the delivery tools and the recovery tool can be influenced by whether or not the embolism protection device remains attached when deployed.

For embodiments in which the device remains attached after delivery, the delivery tool can comprise one or more tubes, sheaths, rigid extensions, wires, strings, filaments, tethers or the like appropriately positioned for extracting the device. In some embodiments, the strings are placed such that pulling on the string tends to contract the device to reduce or eliminate friction on the vessel wall. For example, the strings can be positioned at or near the outer edge of the device that contacts the vessel wall such that pulling on the string tends to pull the exterior of the device toward the center of the vessel. Tethers and the like also can be useful to maintain an embolism protection device at a delivered position within a vessel. Thus, with a tether, guide wire or other attachment structure to maintain the position of the embolism protection device against flow within the vessel, the device may or may not exert significant force against the inner wall of the vessel.

In addition, a recovery tool can comprise a gripping element that grips the device to reduce its dimensions by physical force such that the embolism protection device can be removed through a catheter or the like. Similarly, the device can be twisted in a cork-screw type fashion to decrease the diameter of the device due to the torque and the compressible nature of the polymers. Similar approaches can be used for placement of the devices within a sheath for delivery of the device. In some embodiment, it may be desirable for the embolism protection device to have a smaller porosity toward the vessel wall relative to the porosity away from the vessel wall to reduce the possibility of emboli escaping from the device during the removal of the device from the patient.

For embodiments in which the embolism protection device remains attached after delivery, a tether or other attachment structure remains connected between a component outside from the patient and the embolism protection device itself. This attachment structure can comprise a guidewire, a hypotube, a catheter, or the like or combination of similar structures. If the embolism protection device remains attached, the recovery components do not need to comprise a guidewire since some component remains tethered to the embolism protection device throughout the procedure, and the attachment structure can be used for guiding any subsequent structures. In some attached embodiments, a guidewire or core wire remains attached to the embolism protection device throughout the procedure, so that the same guidewire or core wire is available for delivery and recovery of the device.

Suitable delivery tools and recovery tools are described further in copending U.S. patent application Ser. No. 10/414, 909 to Ogle, entitled "Embolism Protection Device" and U.S. patent application Ser. No. 10/795,131 to Ogle et al., entitled "Fiber Based Embolism Protection Device," both of which are incorporated herein by reference.

Figure 2:
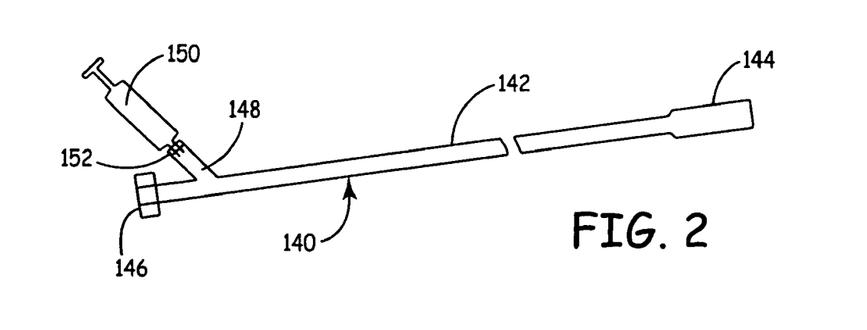
FIG. 2 is a side view of an aspiration catheter with an over the wire design.

Aspiration catheter 124 can comprise an over the wire design or a rapid exchange design. In some embodiments, the aspiration catheter has a compartment at its distal end for withdrawing the embolism protection device from the flow after the filter is retracted from a deployed position. Referring to FIG. 2, aspiration catheter 140 comprises a shaft 142, a distal compartment 144, a proximal end 146, an aspiration connection 148 and a suction device 150. Shaft 142 can have an approximately constant diameter, a varying diameter and/or sections with different diameters. In some embodiments, the average outer diameter of shaft 142 ranges from about 0.010 inches to about 0.065 inches and in additional embodiment from about 0.030 inches to about 0.055 inches. For intervention into blood vessels, shaft 142 generally has a length of at least 20 cm, and in some embodiments from about 50 cm to about 300 cm, and in further embodiments from about 100 cm to about 225 cm. Distal compartment 144 generally has a larger diameter compared with the adjacent section of shaft. In particular, in some embodiments distal compartment 144 has a diameter from about 200 percent to about 110 percent and in further embodiments from about 175 percent to about 120 percent of the average diameter of the ten centimeters of the shaft adjacent distal compartment 144. Distal compartment 144 can have a length from about 0.2 centimeters (cm) to about 3 cm and in further embodiments from about 0.5 cm to about 2 cm. A person of ordinary skill in the art will recognize that additional ranges of sizes are contemplated and are within the present disclosure. The distal compartment or a portion thereof can comprise a radio-opaque marker to provide for visualization using an imaging technique, such as x-ray imaging, for positioning the catheter within the patient.

Proximal end 146 can comprise a handle, ports or other convenient control structures for manipulating aspiration catheter 140 and or the interface of aspiration catheter 140 and other intervention devices. Aspiration connection 148 provides for connection of aspiration catheter 140 with a suction device 150. Aspiration connection 148 can be placed at the proximal end or other location near the proximal end, as convenient. Generally, aspiration connection 148 comprises a fitting 152 or the like to provide a sealed connection with suction device 150. Suitable fittings include, for example, conventional fitting, such as an elastomeric diaphragm through which a syringe needle can be inserted or a Luer lock. Suitable suction devices include, any suction device that can deliver a selected amount of suction, such as a syringe, a compressed bladder, a pump, such as a peristaltic pump or a piston pump, or the like. A tube or the like can be used to connect the suction device to aspiration connection 148.

Aspiration catheter 140 can be formed from one or more biocompatible materials, including, for example, metals, such as stainless steel or alloys, e.g., Nitinol®, or polymers such as polyether-amide block co-polymer (PEBAX®), nylon (polyamides), polyolefins, polytetrafluoroethylene, polyesters, polyurethanes, polycarbonates or other suitable biocompatible polymers. Radio-opacity can be achieved with the addition of markers, such as platinum-iridium or platinum-tungsten or through radio-pacifiers, such as barium sulfate, bismuth trioxide, bismuth subcarbonate, powdered tungsten, powdered tantalum or the like, added to the polymer resin. Generally, different sections of aspiration catheter 140 can be formed from different materials from other sections, and sections of aspiration catheter 140 can comprise a plurality of materials at different locations and/or at a particular location. In particular, it may be desirable to form distal compartment 144 or a portion thereof from an elastomeric polymer, such as suitable polyurethanes, polydimethyl siloxane and polytetrafluoroethylene. In addition, selected sections of the catheter can be formed with materials to introduce desired stiffness/flexibility for the particular section of the catheter. Similarly, fitting 152 can be formed form a suitable material, such as one or more metals and/or one or more polymers.

Figure 3A:
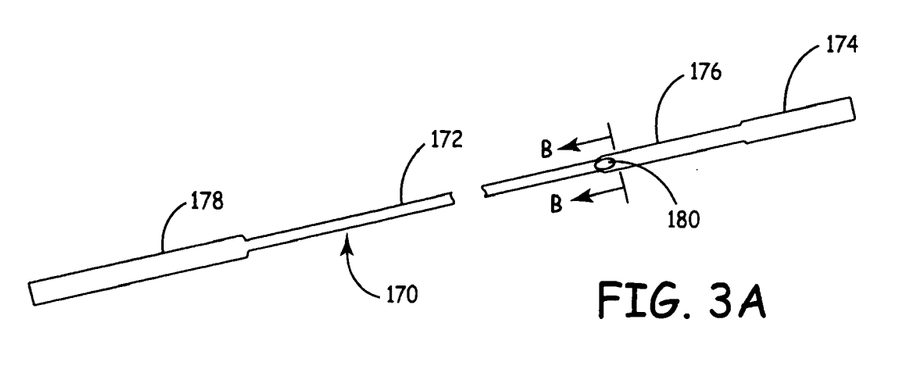
FIG. 3A is a side view of an aspiration catheter with a rapid exchange design.

An embodiment of a rapid exchange aspiration catheter is shown in FIG. 3A. Aspiration catheter 170 has a shaft 172, a distal compartment 174, a rapid exchange segment 176, and proximal portion 178. Since shaft 172 does not ride over a guidewire, shaft 172 can have a smaller diameter than shaft 142 of FIG. 1. Distal compartment 174 generally can have similar characteristics as distal compartment 144 of FIG. 1. Proximal portion 178 can provide for the application of suction through an appropriate connection.

Figure 3B:
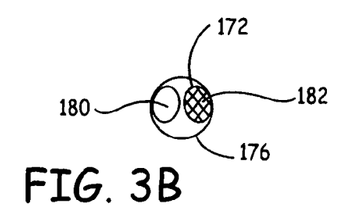
FIG. 3B is a sectional view of an embodiment of the aspiration catheter of FIG. 3A having a grid between a rapid exchange segment and a shaft.
Figure 3C:
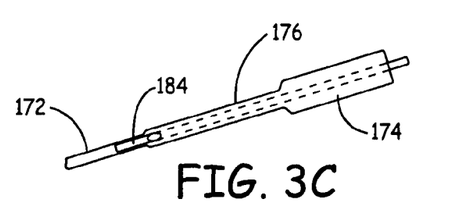
FIG. 3C is a fragmentary side view of an embodiment of the aspiration catheter of FIG. 3A having a tube within a port for directing a guidewire through the port.

In use, rapid exchange segment 176 rides over a guidewire. Therefore, rapid exchange segment 176 generally can have a larger diameter than shaft 172. Guidewire exits through port 180 without blocking suction from shaft 172 that is transmitted to distal compartment 174. To facilitate insertion of the guidewire through port 180, shaft 172 can have a grid 182 at the opening between shaft 172 and rapid exchange segment 176, as shown in FIG. 3B. In some embodiments, a tube 184 is inserted through port 180 to guide insertion of a guidewire through port 180, as depicted in FIG. 3C. Specifically, the guidewire can be inserted through the tube through the port. Then, the tube can be removed for the insertion of the catheter into the patient's vessel.

In some embodiments, rapid exchange segment 176 has a length from about 1 cm to about 35 cm, in further embodiments from about 2 cm to about 30 cm, and in further embodiments from about 5 cm to about 25 cm. The length of the rapid exchange section can be selected to provide desired delivery properties since rapid exchange segment 176 generally is stiffer than shaft 172. Rapid exchange segment generally has an outer diameter from about 0.030 inches to about 0.050 inches, and in some embodiments from about 0.035 inches to about 0.045 inches. A person of ordinary skill in the art will recognize that additional ranges of sizes are contemplated and are within the present disclosure.

Figure 4:
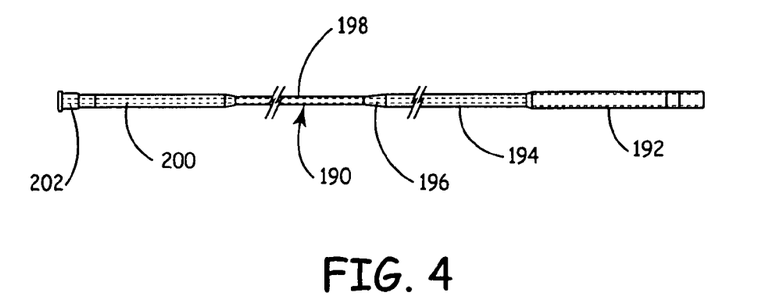
FIG. 4 is a side view of a specific embodiment of a rapid exchange aspiration catheter.

A specific embodiment of a rapid exchange aspiration catheter is shown in FIG. 4. In this embodiment, rapid exchange aspiration catheter 190 has a tubular distal compartment 192 with a length of 1.70 cm, an inner diameter of 0.35 inches and an outer diameter of 0.048 inches. Rapid exchange segment 194 has a length of 18.3 cm and an outer diameter of 0.040 inches. Port 196 is at the interface between rapid exchange segment 194 and shaft 198. Port has a diameter of at least 0.0145 inches for use with a guidewire with a diameter of 0.014 inches. Shaft 198 has a length of 100 cm. Proximal portion 200 is generally cylindrical with a rigid construction. A Luer lock 202 is attached to the proximal end of proximal portion 200. A Luer lock is a fitting that provides for a connection to a syringe and that is conventionally used on intravenous systems and other medical systems.

Figure 5:
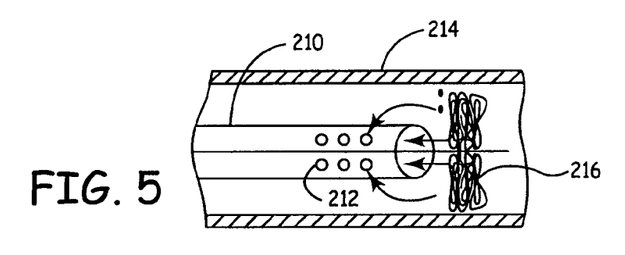
FIG. 5 is a fragmentary side view of an aspiration catheter with side passages near the distal end of the catheter depicted near a deployed embolism protection device.
Figure 6:
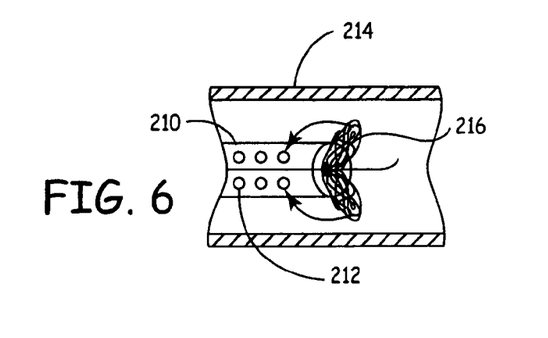
FIG. 6 is a fragmentary side view of the aspiration catheter of FIG. 5 in which the embolism protection device is reconfigured to a recovery configuration for drawing into the distal end of the aspiration catheter.

In some embodiments, the aspiration catheter is designed with specific features to help maintain the suction as the embolism protection device is drawn into the distal end of the aspiration catheter. For example, the distal end can have side ports adjacent the distal end such that a compressed embolism protection device does not block all flow into the catheter. By maintaining the suction, no emboli or fewer emboli are released. Referring to FIGS. 5 and 6, aspiration catheter 210 has side ports 212, which is depicted within vessel 214. As shown with flow arrows, suction can draw fluid through the distal end of catheter 210 or through side ports 212. Six side ports are shown in FIGS. 5 and 6. The size, number (such as 1 port, 2-5 ports, or more than 6 ports), and particular positioning can be determined by a person of ordinary skill in the art for a particular design of embolism protection device to obtain appropriate suction. As shown in FIG. 6, embolism protection device 216 is entering the distal end of aspiration catheter 210.

Figure 7:
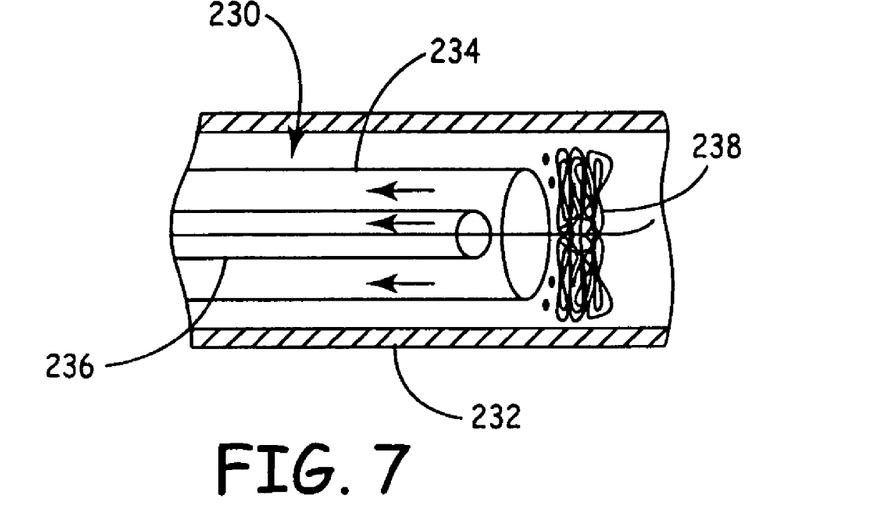
FIG. 7 is a fragmentary side view of an aspiration catheter with a dual lumen depicted near a deployed embolism protection device.
Figure 8:
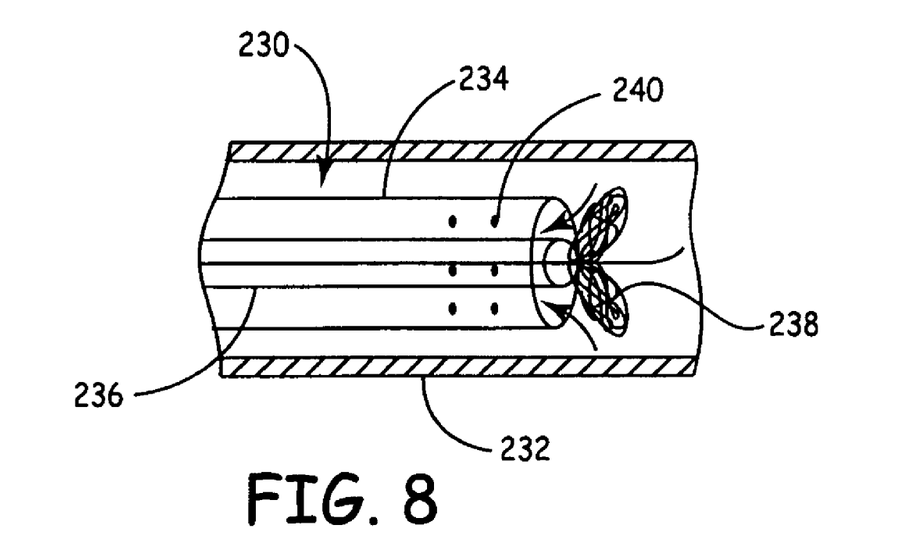
FIG. 8 is a fragmentary side view of the aspiration catheter of FIG. 7 in which the embolism protection device is reconfigured to a recovery configuration for drawing into the distal end of the aspiration catheter.

In additional or alternative embodiments, aspiration catheter has a dual lumen. Referring to FIGS. 7 and 8, aspiration catheter 230, depicted within vessel 232, has an outer sheath 234 and an inner tube 236. During retrieval of embolism protection device 238 is drawn within inner tube 236, as depicted in FIG. 8. Suction generally is applied to both outer sheath 234 and inner tube 236. If suction is blocked into inner tube 234, suction can continue in the lumen of sheath 234 to withdraw emboli 240. The dual lumen structure can extend along the entire length of the aspiration catheter or over just a portion of the length. With dual lumen embodiments, the distal end of both lumens is generally expanded relative to the shaft of the catheter. The spacing between the inner tube and the outer shaft can be selected by a person of ordinary skill in the art to accommodate the embolism protection device while maintaining sufficient suction.

Embolism Protection Devices

The embolism protection devices can have various sizes and shapes both with respect to the effective exterior surface before and after deployment and with respect to the arrangement of the materials through the cross section of the structure. For example, some membrane based filtration embolism protection devices are commercially available. However, embolism protection devices with a three dimensional filtering matrix can provide desirable properties for filtering and removal. A three dimensional filtering matrix provides a flow network with multiple flow pathways that flow through the matrix tends not become occluded as smaller emboli are trapped. In some embodiments, embolism protection devices with three dimensional filtering matrices have an expanding structure that incorporate material, such as hydrogels and/or shape memory fibers. In further embodiments, embolism protection devices incorporate fibers, such as surface capillary fibers, that can be deployed with fibers expanded across the lumen of a patient's vessel to form a three dimensional filtering matrix. Suitable embolism protection devices can be incorporated within an integrated structure for deployment and recovery, with one specific embodiment described below.

An embolus as used herein refers broadly to a particle, besides living cells, in a vessel within a mammal having a diameter of at least about 5 microns. For this determination, the diameter is considered the largest distance between two points on the surface of the particle. Thus, emboli would encompass emboli within the blood as well as kidney stones and the like. Vascular emboli are thought to be composed almost exclusively of clotted blood. Arterial emboli generated in aortic surgery or endovascular intervention can be composed of other components, but it is generally believed that they nearly all contain some component of fibrin. The materials and structure of the device can be selected to have porosity that would allow blood elements, such as white blood cells (about 7-20 microns), red blood cells (8-9 microns) and platelets (2-4 microns), yet collects emboli. In contrast, emboli generally range in size with diameters from about 20 microns to about 3.5 mm, in some embodiments from about 45 microns to about 1000 microns and in further embodiments from about 50 microns to 200 microns. A person of ordinary skill in the art will recognize that additional ranges of emboli within the explicit ranges are contemplated and are within the present disclosure.

Commercially available filtration devices include, for example, the RX Accunet™ Embolic Protection System, available from Guidant, Indianapolis, Ind. This Guidant filter is formed from a nickel-titanium alloy in a mesh. Also, Boston Scientific (Boston, Mass.) markets FilterWire EX™ Embolic Protection System. The Boston Scientific device has a polyurethane filter. See also, U.S. Pat. No. 6,695,813 to Boyle et al., entitled "Embolic Protection Devices," and U.S. Pat. No. 6,391,045 to Kim et al., entitled "Vena Cava Filter," both of which are incorporated herein by reference.

In some embodiments, an embolism protection device can comprise a polymeric substrate (media, sponge), especially an expandable polymer, such as a swelling polymer, a memory polymer or a compressed polymer. Specifically, in some embodiments, the embolism protection devices described herein generally comprise a swelling polymer that expands, generally spontaneously, upon contact with an aqueous solution, such as blood or other body fluids. Swelling is considered broadly in terms of significant changes in dimension due to an absorption or other intake of fluid/liquid into the structure of the material, such as with a sponge, a hydrogel or the like. Hydrogels are generally hydrophylic polymers that are nevertheless not soluble in aqueous solutions. Generally, hydrogels are crosslinked to prevent them from being soluble. Embolism protection devices comprising a swelling polymer, such as hydrogels and/or shape memory fibers, are described further copending U.S. patent application Ser. No. 10/414,909 to Ogle, entitled "Embolism Protection Devices" (now U.S. Pat. No. 7,303,575), incorporated herein by reference. This pending application also describes the delivery of a bioactive agent in conjunction with the embolism protection device.

With respect to the shape of the exterior of the device, this shape can be, for example, generally spherical, cylindrical, concave, or saddle shaped. A generally spherical or other shaped device may nevertheless have a roughly irregular surface contour about an average overall shape, which can orient and adjust to the vessel inside wall upon expansion. Some representative examples are provided below. Any particular device generally can conform to the specific size and shape of the inside of the vessel following a rough size selection for the device. While the particular device size depends on the size of the particular vessel, an embolism protection device following expansion within the vessel of a human patient general can have a diameter perpendicular to the flow direction from about 50 microns to about 35 millimeters (mm), in additional embodiments from about 100 microns to about 9 mm and in further embodiments, from about 500 microns to about 7 mm. A person of ordinary skill in the art will recognize that additional ranges of device diameters within the explicit ranges are contemplated and are within the present disclosure.

In the fiber based embodiments described herein, the outer surface of the device may be only generally defined by extrapolating between neighboring fibers along the outer portions of the structure. The nature of the arrangement of the material across the device generally is formulated to be consistent with the maintenance of flow through the device while capturing emboli over an appropriate size such that they do not flow past the device. Thus, the device can comprise a single fiber that folds to form a particular structure, multiple fibers that are arranged various ways, and the structure can comprise one or more fibers combined with one or more additional materials to form the filtering portion of the embolism protection device. For example, the fibers can be organized into a bundle that is deployed within the vessel. A bundle of fibers may or may not be associated with a fabric cover that mediates the interaction of the fibers with the vessel wall. The embolism protection device can comprise a plurality of domains with one or both of the domains comprising fibers.

Surface capillary fibers (SCF) fibers are characterized by surface channels or capillaries formed within the surface of the fiber. Surface capillaries are characterized by having a portion of the capillary exposed at the surface of the fiber along the length of the fiber. The surface capillaries result in significant increase in the surface area of the fibers relative to fibers with a smooth surface and the same diameter. The surface capillaries generally run along the length of the fiber. In some embodiments, the surface of the fiber has a plurality of surface channels or capillaries along the length of the fiber. An SCF fiber can have surface channels that essentially make up a large fraction of the bulk of the fiber such that little if any of the interior mass of the fiber is not associated with walls of one or more surface capillaries. In particular, the SCF fiber substrate can be formed with a relatively complex cross-sectional geometry. Suitable fibers include commercially available 4DG™ fibers (Fiber Innovation Technology, Inc., Johnson City, Tenn.) but would also include new advanced geometries to provide for greater fluid transport or absorption or wetting capabilities. Suitable approaches for the manufacture of the SCF are described in, for example, U.S. Pat. No. 5,200,248 to Thompson et al., entitled "Open Capillary Structures, Improved Process For Making Channel Structures And Extrusion Die For Use Therein," incorporated herein by reference. Alternative fiber structures are described below.

Embolism protection devices formed from fibers, such as surface capillary fibers, are described further in copending U.S. patent application Ser. No. 10/795,131 to Ogle et al., entitled "Fiber Based Embolism Protection Device" (now U.S. Pat. No. 7,879,062), incorporated herein by reference.

For any of the embolism protection device embodiments, once the embolism protection device is positioned within a vessel, appropriate flow should be maintained through the device while emboli are trapped. Thus, with respect to the flow direction, the device has controlled porosity. This controlled porosity can be established by the nature of the material and/or by the particular structure. Specifically, the fiber density and fiber structure within the device can lead to an effective distribution of pores such that desired flow is provided while emboli are trapped. In particular, SCF fibers can trap smaller emboli within the surface capillaries, while larger emboli can be trapped along the surface and/or between fibers within the overall embolism protection device structure.

In general, the desired filtering properties and corresponding average pore sizes and pore size distributions of an embolism protection device may depend on the particular location of the particular vessel in which it is delivered. However, for many applications it can be desirable to block the flow of a substantial majority of particulates with a diameter of at least about 0.2 mm while allowing the flow of a substantial majority of particulates with a diameter of no more than about 0.001 mm, and in other embodiments, to block the flow of a substantial majority of particulates with a diameter of at least about 0.1 mm while allowing the flow of a substantial majority of particulates with a diameter of no more than about 0.01 mm. A person of ordinary skill in the art will recognize that additional ranges of filtering ability within the explicit ranges are contemplated and are within the present disclosure. A substantial majority of particulates can be considered to be at least about 99 percent.

Figure 9:
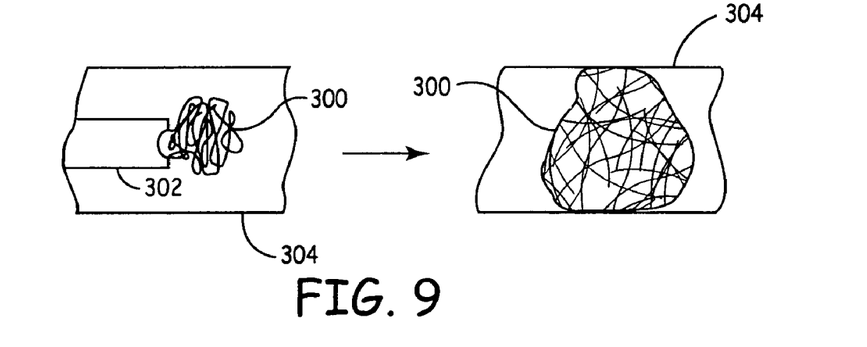
FIG. 9 is a schematic side view of an embolism protection device within a patient's vessel with the left view showing the deployment of the device from a deployment apparatus and the right view showing the device following deployment.
Figure 10:
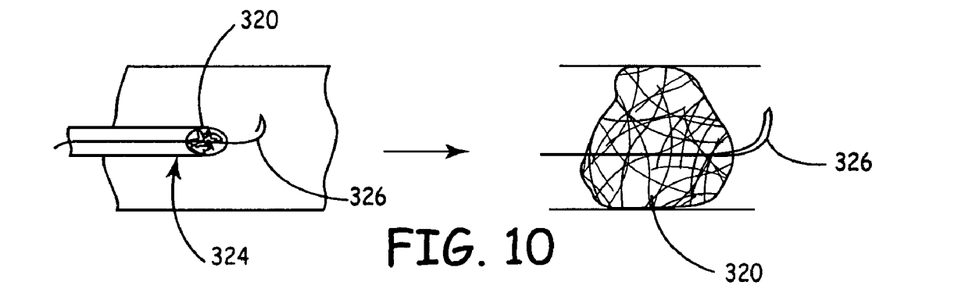
FIG. 10 is a schematic perspective of an alternative embodiment with a fiber matrix being deployed from a sheath using a guidewire.
Figure 11:
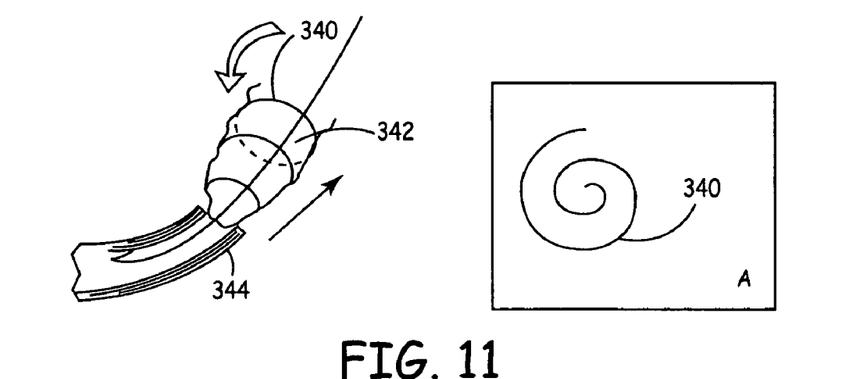
FIG. 11 is a schematic of a tool to compress the embolism protection device to allow loading into a sheath with a top view of the device shown in insert A.

Referring to FIG. 9, the left view displays a generally spherical embolism protection device 300 formed from a fiber mesh adjacent a catheter 302 within a vessel 304. The right hand view in FIG. 9 shows device 300 following expansion to fill the lumen of vessel 304. The arrow between the two views indicates a temporal advance over which device 300 expands across the lumen of vessel 304. In this embodiment, device 300 has a random array of fibrous polymer forming the interior of the device 300. The expansion can be driven by a shape memory of the fibers, although other mechanisms are possible. Referring to an alternative embodiment in FIG. 10, embolism protection device 320 has a generally cylindrical shape with a fiber matrix 322 that is approximately arranged on a grid. The outer surface of the cylinder is covered with fabric 324 with the ends of the cylinder exposed, i.e., free of the fabric. If fabric 324 has a sufficiently open weave, the fabric may also cover the ends of the cylindrical structure. In FIG. 10, the device 320 has a fiber matrix that can be delivered with a sheath 324 using a guide wire 326. As shown in FIG. 11, a spiral device 340 (shown in a top view in insert A) can compress a fiber matrix 342 for loading into a sheath 344. The embolism protection device can be tapered such that an end of the expanded device fits within the sheath. Then, pulling the device relative to the sheath, such as using a tether or other attachment structure, can compress the device within the sheath for removal of the device within the sheath from the patient.

Figure 12:
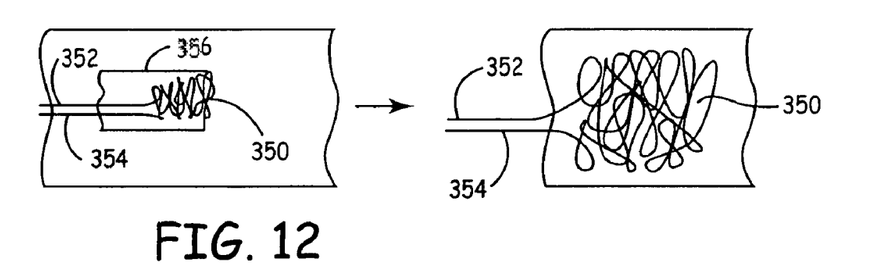
FIG. 12 is a schematic side view of an alternative embodiment of an embolism protection device with a tether to facilitate removal within a patient's vessel with the left view showing the deployment of the device from a deployment apparatus and the right view showing the device following deployment.
Figure 13:
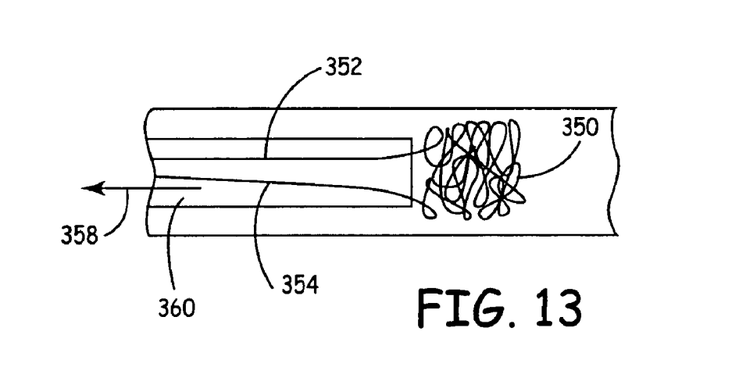
FIG. 13 is a schematic side view showing the use of the tether to remove the device of FIG. 12.
Figure 14:
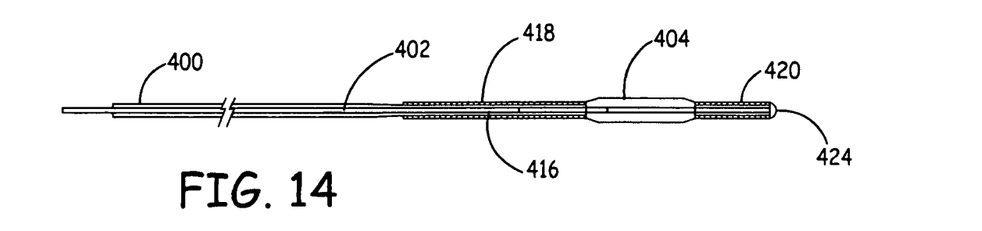
FIG. 14 is a sectional side view of a particular embodiment of an integrated embolism protection device and delivery tool.

An embolism protection device can comprise an attachment structure to facilitate removal of the device after sufficient time to protect against emboli. Referring to FIG. 12, embolism protection device 350 comprises two strings 352, 354 that tether device 350, although a single string or greater than two strings can be used. Device 350 is shown in an unexpanded configuration in the left side view of FIG. 12 within a catheter or hypo tube 356 and in its expanded form in the right side view of FIG. 12. By providing two strings, pulling on the strings tends to draw the strings together to contract the device if the strings are in a spaced apart attachment on the device. As shown in FIG. 13, tension on strings 352, 354, as indicated by arrow 358, is resulting in contraction in diameter of device 350 and corresponding movement from right to left, which can draw device 350 within an aspiration catheter 360. Other configurations of strings can be used to tether an embolism protection device to facilitate removal and to contract the device, which may depend on the particular shape and structure of the device.

Other embolism protection device configurations that can be adapted for fiber based devices are described in copending U.S. patent application Ser. No. 10/414,909 to Ogle, entitled "Embolism Protection Devices," incorporated herein by reference.

As noted above, the embolism protection device can be part of an integrated system to provide for the delivery and/or recovery of the device. In particular, the devices are suitable for placement past an obstruction such that the embolism protection device can be deployed prior to the performance of a procedure on the obstruction. In some embodiments, the integrated apparatus generally comprises a guidewire, a hypotube and the embolism protection device. Relative longitudinal motion of the hypotube over the guide wire can be used to deploy the embolism protection device. In some embodiments, the hypotube is dimensioned for the placement of a treatment structure over the hypotube for treatment of an obstruction.

In some particular embodiments, the guidewire has a length such that the guidewire extends past the distal end of the hypotube while extending also from the proximal end of the hypotube. Generally, the guidewire extends from the proximal end of the hypotube to provide for independent manipulation of the guidewire relative to the hypotube, especially for longitudinal movement and from the distal end for attachment to a medical device such as grippers or an embolism protection device. In general, it is desirable to be able to transfer torque from the hypotube to the guidewire to be able to rotate the tip of the guidewire with less fade of the rotational motion from the proximal end to the distal end of the guidewire. To accomplish this objective, it is possible to rotationally couple the hypotube without prohibiting the longitudinal motion of the hypotube relative to the guidewire. For example, the coupling can be accomplished with a key/keyway interaction, a coil that couples with the application of torque or a compression coupling. The torque coupling of the hypotube and the guidewire is described further in copending U.S. Provisional Patent application Ser. No. 60/550,880 to Picorney et al., filed on Mar. 6, 2004, entitled "Steerable Guide Wire And Shaft With Small Diameters," incorporated herein by reference.

Figure 15:
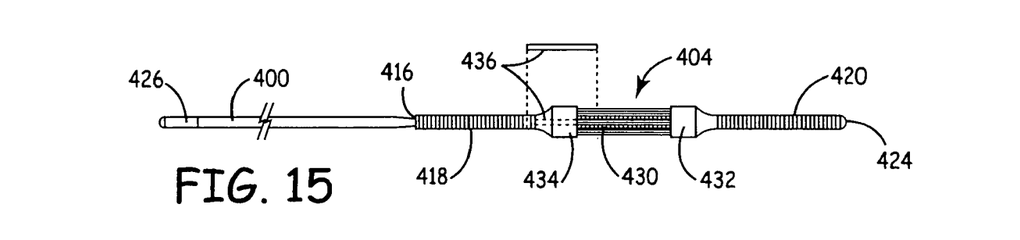
FIG. 15 is a side view of the integrated device of FIG. 14.
Figure 16:
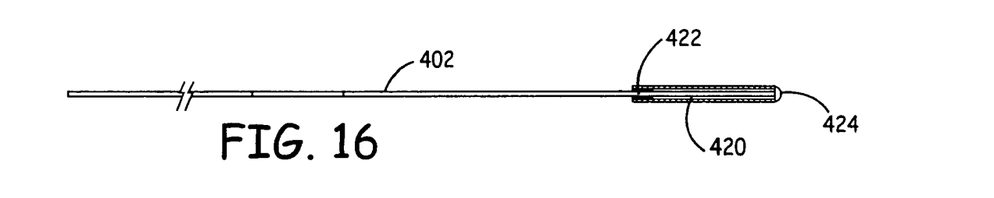
FIG. 16 is a side view of the guidewire of the integrated device of FIG. 14.

One specific embodiment is shown in FIGS. 14-17. In this embodiment, the integrated instrument comprises a hypotube 400, a guidewire 402, and an embolism protection device 404. Referring to the sectional view in FIG. 14 and the side view in FIG. 15, hypotube 400 has a tapered section 416 at its distal end that mimics the taper on a conventional guidewire. A wire coil 418 is located over the tapered section 416. Guidewire 402 is covered with a coil 420 at its distal end, as shown in FIG. 16. Coil 420 is connected with solder 422 and a weld 424, although other attachment approaches can be used. Hypotube 400, guidewire 402, wire coil 418, coil 420 and grip 426 can all be formed from stainless steel, although other suitable materials can be used.

Figure 17:
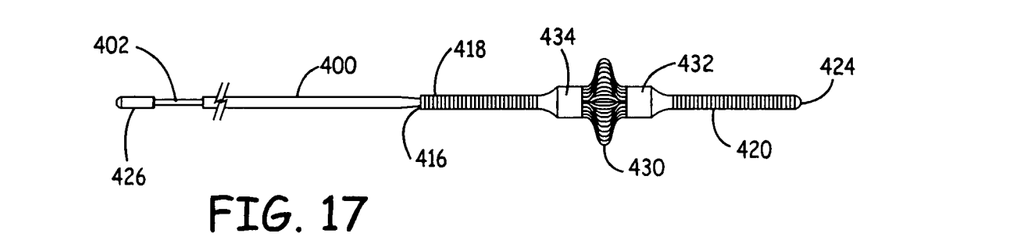
FIG. 17 is a side view of the device of FIG. 14 following expansion of the embolism protection device.

In this embodiment, embolism protection device 404 comprises a bundle of SCF fibers 430 attached at first attachment 432 and second attachment 434, as shown in FIGS. 15 and 17. Bundle of fibers 430 are collected in a generally cylindrical configuration for delivery into the vessel, as shown in FIG. 15. A 0.1 inch long tube 436, which can be formed from polyimide polymer, is located within the second attachment 434 with guidewire 402 extending within the tube. The fibers are swaged/crimped at the two attachments 432, 434 to a diameter of 0.033 inches with radio-opaque bands. After crimping, the fiber bundles are bonded at each end with an adhesive, such as cyanoacrylate.

The number of fibers in the bundle generally depends on the desired degree of filtration as well as the thickness of the fibers. In general, the number of fibers can be range from at least 10 fibers, in further embodiments from 25 fibers to 1,000,000 fibers, in other embodiments from 50 fibers to 10,000 fibers and in additional embodiments, from 100 fibers to 5,000 fibers. The length of the fibers can be selected based on the size of the corresponding vessel. When deployed, the centers of the fibers are projected across the lumen of the vessel. Thus, the unconstrained length of the fibers between attachment structures 432, 434 should be at least double the radius of the vessel. In some embodiments relating to the use of a plurality of fibers to expand within the lumen of a patient's vessel, it is generally appropriate to use fibers that have a length from about 2.2 to about 10 times the vessel radius, in some embodiments from about 2.4 to about 5 times the vessel radius and in further embodiments front about 2.6 to about 4 times the vessel radius. For placement in a human vessel, the fibers generally have a length from about 0.5 mm to about 100 mm, in other embodiments from about 1 mm to about 25 mm, and in further embodiments from about 2 mm to about 15 mm. A person of ordinary skill in the art will recognize that additional ranges of fiber numbers and fiber length within the explicit ranges are contemplated and are within the present disclosure. In one specific embodiment, the device comprises 480-6 denier SCF fibers in a bundle and a crossing profile of 0.033 inches (2.5 French).

Use of Aspiration Catheter and Removal of Embolism Protection Devices

In general, the aspiration catheters described herein can be used for a variety of procedures. However, the aspiration catheters are particularly useful for the removal of an embolism protection device from the vessel of a patient. In particular, the aspiration can be effective to capture any emboli that may be released while the embolism protection device is being converted from a deployed orientation to an appropriate orientation for removal. To stabilize the recovery process, the embolism protection device can be drawn into a sheath, generally a distal compartment of the aspiration catheter. Once the embolism protection device is comfortably within the distal compartment of the aspiration catheter, the risk of release of emboli is sufficiently reduced that the suction can be stopped and the embolism protection device safely withdrawn. Thus, by drawing the embolism protection device into a distal compartment of the catheter, the disruption of flow from the suction can be kept to a level such that a shunt for the flow is not used. Radio-opaque markers can be used for positioning during the various steps of the process.

In general, it is desirable to keep the time for the application of suction to lower values to avoid undesirable disruption of the flow through the vessels. Using the improved embolism protection devices described herein and in copending applications cited herein, procedures can be safely performed without blocking the flow through the patient's vessel. Similarly, the use of an embolism protection device with a three dimensional matrix provides for removal of the device into the aspiration catheter without blocking suction into the catheter through flow through the matrix and/or by having a recovery configuration that does not block flow, although a side port in the catheter can complement aspiration through the distal tip of the catheter. Depending on the vessel, the amount of disruption of the flow that can be safely tolerated can be estimated, such that the process for the recovery of the embolism protection device can be accordingly determined. To keep disruption of the flow to lesser levels, the suction generally is applied starting shortly before the recovery process begins. Suction generally can be maintained during the constriction of the device configuration for fitting within the distal compartment and while the device is drawn within the distal compartment. The suction generally is stopped once the device is within the distal compartment and the device is not moved relative to the aspiration catheter. Once the device is safely within the distal compartment, the aspiration catheter can be removed from the patient along with the embolism protection device.

To draw the embolism protection device within the distal compartment of the aspiration catheter, the embolism protection device can be converted from a deployed configuration across the vessel lumen to a recovery configuration, generally with a reduced area across the cross section of the vessel lumen, in which the device fits within the distal compartment of the catheter. By directly converting the embolism protection device to a recovery configuration, the embolism protection device can be formed without structural elements, such as metal struts, to facilitate the mechanical collapse of the device through pressure against the catheter end. This change of configuration can be accomplished with an actuation element that directly converts the device between different configurations. The recovery configuration may or may not be similar to the delivery configuration. A specific embodiment with an actuation element that transforms the embolism protection device between delivery configuration to a deployed configuration and then to a recovery configuration. In other embodiments, some type of gripping or engaging tool can be used to mechanically compress the embolism protection device to a recovery configuration. In additional embodiments, the process of drawing of the embolism protection device into the distal compartment can compress the embolism protection device into the recovery configuration. To facilitate this mechanical compression, the end of the distal compartment can be tapered and/or the proximal end of the embolism protection device can be tapered to facilitate the entrance of the initial portion of the device into the compartment. Thus, the transformation into the recovery configuration and the loading of the device into the distal compartment can be simultaneous steps or sequential steps.

The overall timing of the recovery process involves a balance between several factors within the overall objective of keeping the period of application of suction within desired ranges. To meet the objectives, it is desirable to transform the embolism protection device to the recovery configuration and load the embolism protection device into the distal compartment relatively quickly. However, sharp impacts or abrupt motions of the device raise the possibility of releasing emboli. Therefore, the loading of the device can be performed as quickly as possible with a smooth motion. In general, it is desirable for the total time to transform the device to the recovery configuration and to load the device within the distal compartment to be no more than about five minutes, in other embodiments, no more than about 3 minutes, in additional embodiments from about 2 seconds to about 2 minutes and in further embodiments from about 5 seconds to about 1.5 minutes. Generally, the suction is not applied for more than about 10 seconds, in some embodiments no more than about 5 seconds and in further embodiments no more than about 2 seconds prior to commencing the transformation of the device to the recovery configuration. Similarly, the suction generally is applied for no more than about 10 second, in some embodiments no more than about 5 seconds and in further embodiment no more than about 2 seconds after the embolism protection device is loaded into the distal compartment. A person of ordinary skill in the art will recognize that additional ranges of times within the explicit ranges above are contemplated and are within the present disclosure.

The suction is contrary to the flow within the vessel with is otherwise relatively unrestricted. The suction rate can be greater than the flow within the vessel or some fraction of the flow. Specifically, the suction rate can be no more than about 125 percent of the vessel flow, in further embodiments, no more than about 110 percent of the vessel flow, in further embodiments from about 25 percent to about 100 percent and in additional embodiments from about 50 percent to about 80 percent of the unrestricted flow through the vessel. As a particular example, if the unrestricted flow through the aorta is 5 liters per minute, the suction rate can be 125 percent of the flow or 6.25 liters per minute or the suction rate can be 25 percent of the flow or 1.25 liters per minute. A person of ordinary skill in the art will recognize that additional ranges of flow rates and flow percentages are contemplated and are within the present disclosure. If the suction rate is greater than the natural flow rate, the suction tends to draw fluid from both sides of the embolism protection device into the aspiration catheter. If the suction rate is less than the natural flow rate, the suction tends to draw fluid from the portion of the vessel adjacent the opening of the aspiration catheter. The suction rate can be selected to balance the disruption of the flow with the collection rate for any released emboli. In some embodiments, the flow rate can change at different points in the recovery process. For variable suction rate embodiments, the suction rate is generally greater at the start of the recovery process and reduced once the device is collapsed to a recovery configuration.

Figure 18:
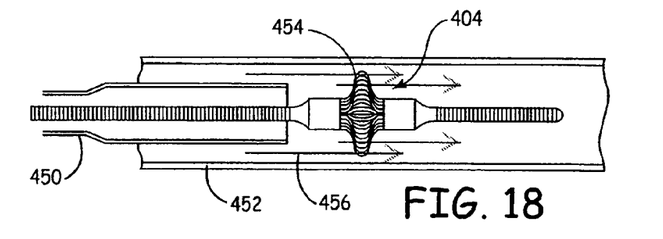
FIG. 18 is a side view of an aspiration catheter positioned within a patient's vessel adjacent a deployed embolism protection device of FIGS. 14-17.
Figure 19:
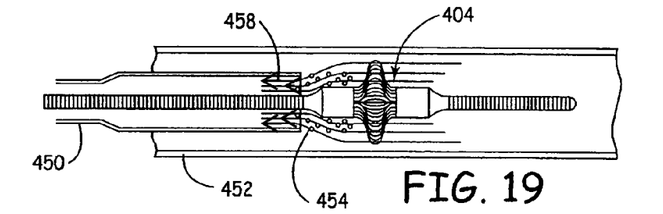
FIG. 19 is a side view of the aspiration catheter of FIG. 18 with suction being applied.
Figure 20:
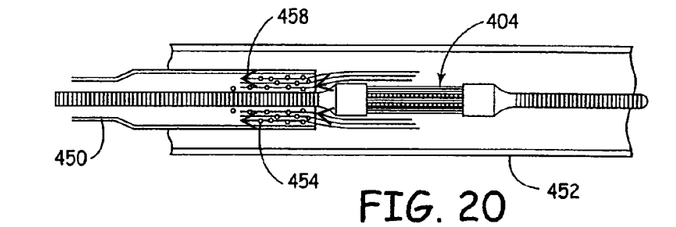
FIG. 20 is a side view of the aspiration catheter of FIG. 18 with suction being applied and with the embolism protection device converted to a recovery configuration.
Figure 21:
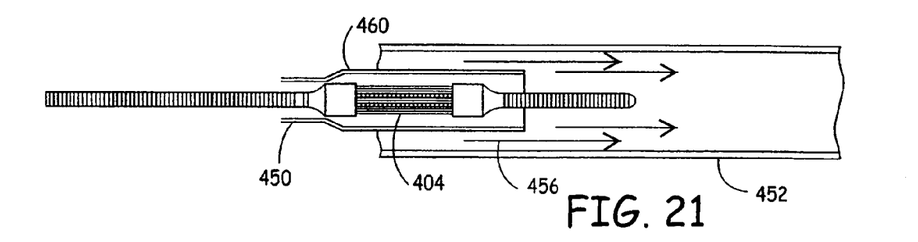
FIG. 21 is side view of the aspiration catheter of FIG. 18 with the embolism protection device within a distal compartment of the aspiration catheter.

FIGS. 18-21 depict the recovery of the embolism protection device of FIGS. 14-17. FIG. 18 depicts an aspiration catheter 450 within a patient's vessel 452 a short distance upstream from embolism protection device 404. Emboli 454 are schematically depicted within device 404 and along the upstream surface of the device. Flow through the vessel is depicted with flow arrows 456. As shown in FIG. 19, suction is applied just before embolism protection device 404 is reconfigured to a recovery configuration. Flow from the suction is depicted with flow arrows 458. FIG. 20 depicts embolism protection device 404 reconfigured to a recovery configuration. Suction is still being applied. Referring to FIG. 21, embolism protection device 404 is withdrawn into distal compartment 460 of aspiration catheter 450. Suction has been turned off in FIG. 21 with essentially unrestrained flow restored in vessel 45

Distribution of Medical Devices

The medical devices described herein are generally packaged in sterile containers for distribution to medical professionals for use. The articles can be sterilized using various approaches, such as electron beam irradiation, gamma irradiation, ultraviolet irradiation, chemical sterilization, and/or the use of sterile manufacturing and packaging procedures. The articles can be labeled, for example with an appropriate date through which the article is expected to remain in fully functional condition.

Various devices described herein can be packaged together in a kit for convenience. For example, an aspiration catheter can be packaged along with an integrated system for delivery and recovery of an embolism protection device. The kit can further include, for example, labeling with instruction for use and/or warnings, such as information specified for inclusion by the Food and Drug administration. Such labeling can be on the outside of the package and/or on separate paper within the package.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What we claim is:

1. A method for removing a filtration device from a patient's vessel lumen through an aspiration catheter, the method comprising:

(a) converting a bundle of at least 50 surface capillary fibers of the filtration device from an expanded configuration having a diameter spanning the vessel lumen to a reduced diameter configuration while applying suction through an opening at a distal end of the aspiration catheter located proximal to the filtration device such that debris captured in the bundle of fibers is drawn into the aspiration catheter, wherein the converting step comprises changing the relative position of a corewire and a hypotube that the corewire runs within such that a first end of the bundle of fibers attached to move with the core wire and a second end of the bundle of fibers attached to move with the hypotube move apart from each other, wherein in the reduced diameter configuration, the fibers are all substantially aligned with each other, and wherein in the expanded configuration, an unconstrained portion of the bundle of fibers flares with respect to the reduced diameter configuration to form a porous filter matrix;

(b) after converting the filtration device to the reduced diameter configuration, drawing the filtration device into the aspiration catheter while applying suction therethrough, and (c) removing the aspiration catheter from the vessel with the filtration device disposed within the catheter.

2. The method of claim 1 wherein the suction is applied with a syringe.

3. The method of claim 1, wherein the step of applying suction through the aspiration catheter is applied at a suction rate greater than an unrestricted natural flow rate of fluid in the patient's vessel and in an opposite direction of the fluid flow.

4. The method of claim 3, wherein the suction rate greater than the unrestricted flow rate of the fluid causes the aspiration catheter to draw fluid from a proximal side of the filtration device and a distal side of the filtration device.

5. The method of claim 3, wherein the suction rate is between approximately 100 percent and 125 percent of the unrestricted natural fluid flow rate.

6. The method of claim 1, wherein the step of applying suction through the aspiration catheter is begun prior to the step of converting the filtration device from the expanded configuration to the reduced diameter configuration.

7. The method of claim 6, wherein the step of applying suction through the aspiration catheter is begun no more than ten seconds prior to the step of converting the filtration device from the expanded configuration to the reduced diameter configuration.

8. The method of claim 6, wherein the step of applying suction through the aspiration catheter prior to the converting step causes debris captured in the filter matrix to be drawn into the aspiration catheter.

* * * * *